US010507027B2

(12) United States Patent
Fetzer et al.

(10) Patent No.: US 10,507,027 B2
(45) Date of Patent: Dec. 17, 2019

(54) PUSH BUTTON RONGEUR

(71) Applicant: Boss Instruments Ltd., Inc., Gordonsville, VA (US)

(72) Inventors: Berndt Fetzer, Schaumburg, IL (US); Peter Fetzer, Oehningen-Wangen (DE)

(73) Assignee: BOSS INSTRUMENTS, LTD., INC., Gordonsville, VA (US)

( * ) Notice: Subject to any disclaimer, the term of this patent is extended or adjusted under 35 U.S.C. 154(b) by 189 days.

(21) Appl. No.: 15/837,697

(22) Filed: Dec. 11, 2017

(65) Prior Publication Data

US 2018/0116680 A1 May 3, 2018

Related U.S. Application Data

(63) Continuation-in-part of application No. 14/419,344, filed as application No. PCT/US2013/053192 on Aug. 1, 2013, now Pat. No. 9,867,626.

(60) Provisional application No. 61/679,316, filed on Aug. 3, 2012.

(51) Int. Cl.
*A61B 17/00* (2006.01)
*A61B 17/16* (2006.01)
*A61B 90/00* (2016.01)

(52) U.S. Cl.
CPC ...... *A61B 17/1608* (2013.01); *A61B 17/1611* (2013.01); *A61B 2090/0813* (2016.02)

(58) Field of Classification Search
CPC combination set(s) only.
See application file for complete search history.

(56) References Cited

U.S. PATENT DOCUMENTS

| 3,842,839 A | 10/1974 | Malis et al. |
| 4,499,899 A | 2/1985 | Lyons, III |
| 4,545,374 A | 10/1985 | Jacobson |
| 4,722,338 A | 2/1988 | Wright et al. |
| 4,733,633 A | 3/1988 | Farley |
| 4,770,174 A | 9/1988 | Luckman et al. |
| 4,990,148 A | 2/1991 | Worrick, III et al. |
| 5,009,661 A | 4/1991 | Michelson |
| 5,026,375 A | 6/1991 | Linovitz et al. |
| 5,061,269 A | 10/1991 | Muller |
| 5,273,519 A | 12/1993 | Koros et al. |
| 5,312,407 A | 5/1994 | Carter |
| 5,439,464 A | 8/1995 | Shapiro |
| 5,451,227 A | 9/1995 | Michelson |
| 5,484,441 A | 1/1996 | Koros et al. |

(Continued)

FOREIGN PATENT DOCUMENTS

| CA | 2007589 | 7/1990 |
| CA | 2117220 | 9/1994 |

(Continued)

OTHER PUBLICATIONS

International Search Report & Written Opinion from International Patent Application No. PCT/US2013/053192 dated May 27, 2016.

(Continued)

*Primary Examiner* — Sameh R Boles
(74) *Attorney, Agent, or Firm* — Nixon & Vanderhye, P.C.

(57) ABSTRACT

Disclosed is a Rongeur for surgical use. The disclosed Rongeur has a push button actuator which, upon activation, allows the long parts of the Rongeur to be easily separated for thorough cleaning and sterilization for reuse.

15 Claims, 6 Drawing Sheets

(56) References Cited

U.S. PATENT DOCUMENTS

| | | |
|---|---|---|
| 5,569,258 A | 10/1996 | Gambale |
| 5,584,844 A | 12/1996 | Weisshaupt |
| 5,584,855 A | 12/1996 | Onik |
| 5,653,713 A | 8/1997 | Michelson |
| 5,766,177 A | 6/1998 | Lucas-Dean et al. |
| 5,851,214 A | 12/1998 | Larsen et al. |
| 5,961,531 A * | 10/1999 | Weber ............... A61B 17/1611 604/22 |
| 6,129,740 A | 10/2000 | Michelson |
| 6,142,997 A | 11/2000 | Michelson |
| 6,200,320 B1 | 3/2001 | Michelson |
| 6,214,010 B1 | 4/2001 | Farley et al. |
| 6,478,805 B1 | 11/2002 | Marino et al. |
| 6,575,977 B1 | 6/2003 | Michelson |
| 6,609,322 B1 | 8/2003 | Michelson |
| 6,638,280 B2 | 10/2003 | Agbodoe |
| 6,685,710 B2 | 2/2004 | Agbodoe et al. |
| 6,695,849 B2 | 2/2004 | Michelson |
| 6,699,254 B1 | 3/2004 | Tontarra |
| 6,723,103 B2 | 4/2004 | Edwards |
| 6,991,633 B2 | 1/2006 | Agbodoe |
| 7,011,663 B2 | 3/2006 | Michelson |
| 7,014,638 B2 | 3/2006 | Michelson |
| 7,297,147 B2 | 11/2007 | Michelson |
| 7,615,053 B2 | 11/2009 | McKinley |
| 7,691,107 B2 | 4/2010 | Schneiter |
| 7,922,723 B2 | 4/2011 | Michelson |
| 7,988,699 B2 | 8/2011 | Martz et al. |
| 2001/0005786 A1 | 6/2001 | Michelson |
| 2001/0031221 A1 | 10/2001 | Wu et al. |
| 2003/0069583 A1 | 4/2003 | Agbodoe et al. |
| 2003/0069584 A1 | 4/2003 | Agbodoe |
| 2003/0187450 A1 | 10/2003 | Agbodoe |
| 2003/0216740 A1 | 11/2003 | Michelson |
| 2004/0035903 A1 | 2/2004 | Michelson |
| 2004/0044346 A1 | 3/2004 | Boury |
| 2004/0049200 A1 | 3/2004 | Edwards |
| 2004/0102783 A1 | 5/2004 | Sutterlin, III et al. |
| 2004/0122433 A1 | 6/2004 | Loubens et al. |
| 2004/0186499 A1 | 9/2004 | Michelson |
| 2006/0095043 A1 | 5/2006 | Martz et al. |
| 2006/0122615 A1 | 6/2006 | McKinley |
| 2006/0149271 A1 | 7/2006 | Michelson |
| 2006/0189995 A1 | 8/2006 | Lancial |
| 2007/0093843 A1 | 4/2007 | Schneiter |
| 2008/0255563 A1 | 10/2008 | Farr et al. |
| 2009/0062805 A1 | 3/2009 | Casutt |
| 2009/0309998 A1 | 12/2009 | Grosvenor et al. |
| 2010/0198222 A1 | 8/2010 | Schneiter |
| 2011/0172647 A1 | 7/2011 | Wenzler et al. |
| 2011/0190773 A1 | 8/2011 | Michelson |
| 2011/0213369 A1 | 9/2011 | Weaver |
| 2012/0010622 A1 | 1/2012 | Heinemann |

FOREIGN PATENT DOCUMENTS

| | | |
|---|---|---|
| CA | 2169740 | 2/1995 |
| CA | 2159685 | 4/1996 |
| CA | 2205014 | 5/1996 |
| CA | 2407023 | 4/2003 |
| CA | 2462483 | 9/2004 |
| DE | 4316768 | 11/1994 |
| DE | 10 2009 006 689 | 10/2009 |
| EP | 243 803 | 11/1987 |
| EP | 244 491 | 11/1987 |
| EP | 378 433 | 7/1990 |
| EP | 614 647 | 9/1994 |
| EP | 706 780 | 4/1996 |
| EP | 1 302 168 | 4/2003 |
| EP | 1 419 741 | 5/2004 |
| EP | 1 464 291 | 10/2004 |
| EP | 1 525 853 | 4/2005 |
| EP | 2 213 254 | 8/2010 |
| GB | 2 198 950 | 6/1988 |
| JP | 2003-164460 | 6/2003 |
| JP | 2004-298636 | 10/2004 |
| JP | 2004-321832 | 11/2004 |
| JP | 2005-118606 | 5/2005 |
| JP | 2010-035669 | 2/2010 |
| WO | 94/26180 | 11/1994 |
| WO | 95/05123 | 2/1995 |
| WO | 96/14799 | 5/1996 |
| WO | 99/65396 | 12/1999 |
| WO | 00/62683 | 10/2000 |
| WO | 02/062240 | 8/2002 |
| WO | 2004/049956 | 6/2004 |
| WO | 2006/044920 | 4/2006 |
| WO | 2006/062555 | 6/2006 |
| WO | 2007/085628 | 8/2007 |
| WO | 2008/039696 | 4/2008 |
| WO | 2008/058070 | 5/2008 |

OTHER PUBLICATIONS

Extended European Search Report from European Patent Application No. 13825313.3 dated May 27, 2016.

* cited by examiner

PUSH BUTTON RONGEUR

RELATED APPLICATIONS

This application is a Continuation-in-Part of U.S. application Ser. No. 14/419,344 filed Feb. 3, 2015, which is the National Stage of International Application No. PCT/US2013/053192 filed Aug. 1, 2013, which claims the benefit to U.S. Provisional Application No. 61/679,316 filed Aug. 3, 2012.

GOVERNMENT SUPPORT

None.

FIELD OF THE INVENTION

The present invention relates generally to the field of medical instruments. Specifically, the present invention relates to an improved Rongeur having a push button actuator to allow the separation of its long parts to facilitate improved cleaning and sterilization.

DESCRIPTION OF THE RELATED ART

In surgical procedures, a Rongeur is used to remove a small amount of tissue or bone material. Critical to the reuse of Rongeurs in successive procedures is the need to thoroughly clean the instrument of biological material and other contamination so as to thoroughly sterilize the instrument. A number of Rongeurs have been developed to facilitate the cleaning and sterilization of their various components. Designs for these Rongeurs include making them able to be disassembled, cleaned and sterilized, and reassembled for subsequent use. This requires skilled technicians and an extended time for cleaning. More recently, a Rongeur has been developed (U.S. Pat. No. 5,961,531, Weber) which allows the long parts of the Rongeur to be totally separated from each other such that the top long part of the Rongeur remains attached at an obtuse angle to the body of the Rongeur by an attachment means. While this is clearly an improvement over Rongeurs requiring disassembly and reassembly, it presents a complex design requiring, among other things, the release of its drive pin from its driving slot.

Accordingly, there is a need for a Rongeur that is simplified in structure with fewer parts, yet facilitates cleaning and sterilization for subsequent use by allowing direct access to the long parts of the Rongeur.

SUMMARY OF THE INVENTION

The present invention is directed to a Rongeur with a simpler, more elegant design with fewer parts which allows direct access to the parts in need of cleaning and sterilization by allowing the separation of those parts with a push button actuator.

In the present disclosure, a Rongeur is presented having a fixed bottom shaft and a movable top shaft (the long parts). The top shaft is slideably connected to and axially aligned with the fixed bottom shaft. The top shaft has a distal end with a cutting portion and a proximal end containing a cavity across which a drive pin is connected. Once the Rongeur is assembled, the drive pin remains captured by the driving hole of the front handle. When the push button actuator is activated, the movable top shaft is retracted slightly to allow the separation of the movable top shaft from the fixed bottom shaft to an acute angle there between. This allows full and direct access to the long parts for cleaning and sterilization.

Some embodiments of the present approach may take the form of a Rongeur with a top shaft with a proximal end having a cutting edge and a distal end hingedly connected to a front handle, the top shaft configured for sliding engagement with a bottom shaft having a rear handle at a distal end, the front handle pivotally connected to the rear handle and configured for a retracted position, a first extended position, and a second extended position. The retracted position may be configured to slide the top shaft proximally such that the cutting edge approaches a proximal end of the bottom shaft. The first extended position may be configured to slide the top shaft distally a first distance. The second extended position may be configured to slide the top shaft distally a second distance greater than the first distance. The Rongeur may have a push button actuator having a biased position and an actuated position, the biased position configured to block the second extended position, and the actuated position configured to permit the second extended position. Some embodiments may incorporate a slot and corresponding protrusion that form a sliding connection between the top and bottom shafts. In some embodiments, for example, the Rongeur has a bottom shaft comprising at least one slot which is configured to receive at least one corresponding protrusion, wherein the corresponding protrusion extends away from a bottom surface of the top shaft. In some embodiments, the protrusion is T-shaped. In some embodiments, the push button actuator includes a groove configured to receive a portion of the front handle when in the actuated position. The push button actuator may include a compression spring which maintains the push button actuator in a normal position while the Rongeur is in use and which is depressed to activate the push button actuator. The Rongeur may have a front handle that includes a drive hole on its proximal end. The drive hole may be elongated to allow movement of a drive pin attached to the top shaft while the top shaft is in a released position. The drive pin may remain in the drive hole while the Rongeur is in use and when the top shaft is separated from the bottom shaft.

While the present invention is directed to a more simplified Rongeur requiring fewer parts, while facilitating cleaning and sterilization, it may apply to various other specific types of Rongeurs. Moreover, the present invention also applies to other types of medical instruments that have inaccessible surfaces that are difficult to properly clean or sterilize.

DETAILED DESCRIPTION OF THE INVENTION

Figure 1:
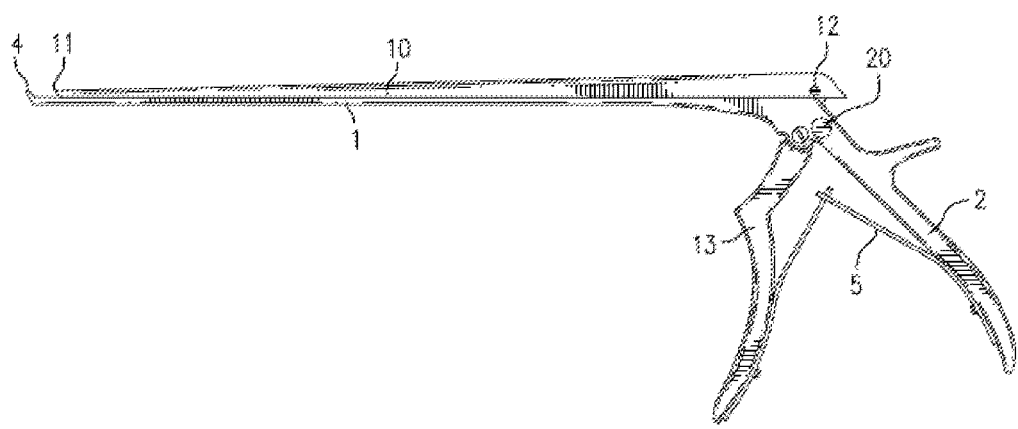
FIG. 1 is a perspective view of an embodiment of the Rongeur in cutting position ready for use.
Figure 2A:
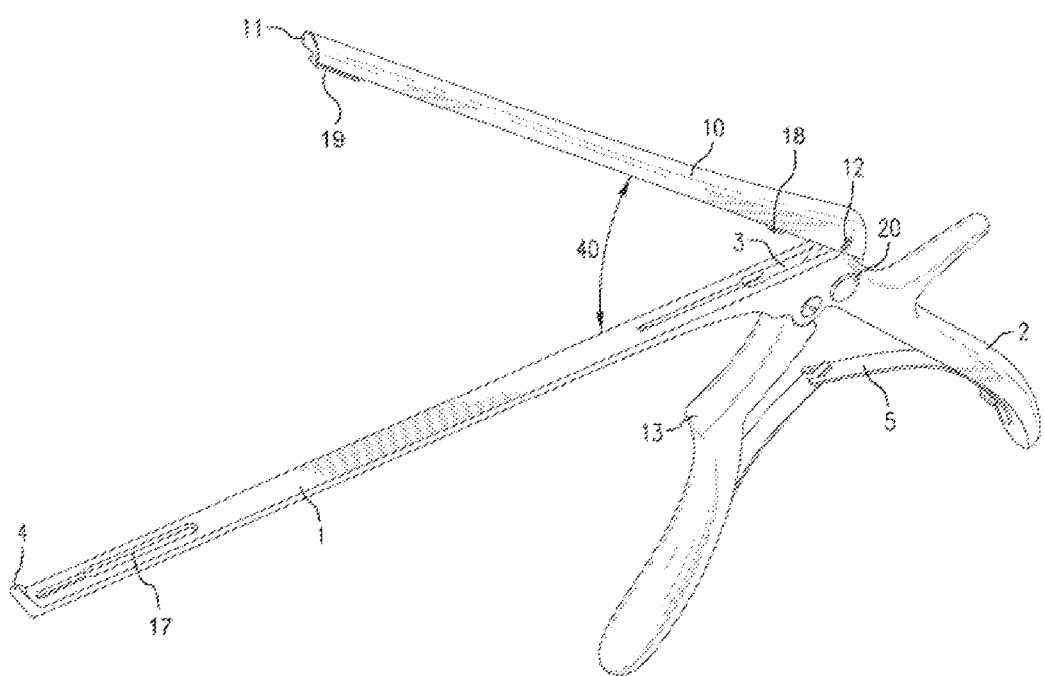
FIG. 2A is a perspective view of an embodiment of the Rongeur with the moveable top shaft separated at an acute angle from the fixed bottom shaft and ready for cleaning.

FIG. 1 shows a preferred embodiment of the disclosed invention in which top shaft (10) is in a normal cutting position relative to fixed bottom shaft (1), ready for use. Top shaft (10) is slideably connected to, and axially aligned with fixed bottom shaft (1). Top shaft (10) has a proximal end with a cutting edge (11) and a distal end containing a cavity (9) (shown in FIG. 2B) orthogonally transversed by drive pin (12). Fixed bottom shaft (1) has a proximal end with a foot plate (4) and a distal end forming rear handle (2). At the transition of bottom shaft (1) to rear handle (2) lies the interaction of front handle (13) with fixed bottom shaft (1) and push button actuator (20). Front handle (13) is pivotally attached to rear handle (2) and is held in the open or normal position by lever spring (5). Lever spring (5) resists against the compression of front handle (13) toward rear handle (2) and keeps the Rongeur in normal position. Top shaft (10), when slidingly engaged with fixed bottom shaft (1) as shown in FIG. 1, may be retracted slightly by depressing the push button actuator (20) which allows the separation of top shaft (10) from fixed bottom shaft (1) to at least an acute angle (40) (shown in FIG. 2A). Also shown in FIG. 2A, is slot (3) which is medially centered on fixed bottom shaft (1) at its transition to rear handle (2). The separation of top shaft (10) from fixed bottom shaft (1) at angle (40) allows direct access to all surfaces of the long parts of the Rongeur for cleaning and sterilization. Once cleaning and sterilization occurs, simply returning top shaft (10) to slideable connection with fixed bottom shaft (1) returns Rongeur to fully operable condition and ready for the next use.

Some embodiments may include a slot and corresponding protrusion that form a sliding connection between the top and bottom shafts. One shaft may include a slot, and another shaft may include a protrusion configured to be received in the shaft. When the slot and protrusion are mated, the top and bottom shafts may slide axially, but the cross-sectional shape of the shaft and the protrusion may be configured to retain the protrusion within the shaft. For example, both may have a T-shape. It should be appreciated that other shapes may be used. This interlocking configuration prevents the top shaft from disconnecting. The shaft may include a wide region configured to allow the protrusion to exit the slot, such as when it is desired to release the top shaft for cleaning purposes. FIG. 2A shows an embodiment in which distal slot (3) in bottom shaft (1), which is configured to receive a distal protrusion (18) which extends away from a bottom surface of top shaft (10) toward bottom shaft (1). Bottom shaft (1) includes proximal slot (17) which is configured to receive proximal protrusion (19), which in this embodiment extends away from a bottom surface of top shaft (10). It should be appreciated that the relative locations of protrusions and slots may vary in other embodiments. Protrusion (18) and protrusion (19) are configured to permit the top shaft (10) to slideably engage with bottom shaft (1), when the top shaft is in the closed position. Proximal slot (17) includes a wide region, sized and shaped to allow protrusion (19) to release from slot (17) if the top shaft (10) is in a released position and hinged open at the hinged connection. It should be appreciated that when the top shaft is returned to the closed position, the distal protrusion (19) returns into distal slot (17) through the wide region, reestablishing the slideable engagement. In this embodiment, slot 3 also includes a wide portion. In some embodiments, the top shaft comprises (10) comprises at least one protrusion (18). In some embodiments, protrusion (18) and protrusion (19) are T-shaped protrusions. It should be appreciated that the cross-sectional shape may vary in other embodiments. For example, in some embodiments, protrusion (18) and protrusion (10) may be Y-shaped, clover-shaped, etc., and may have different shapes in the same embodiment. It should be appreciated that the specific protrusion numbers and shapes shown are demonstrative, and that the scope of the present approach is not limited to only the structures shown.

Figure 2B:
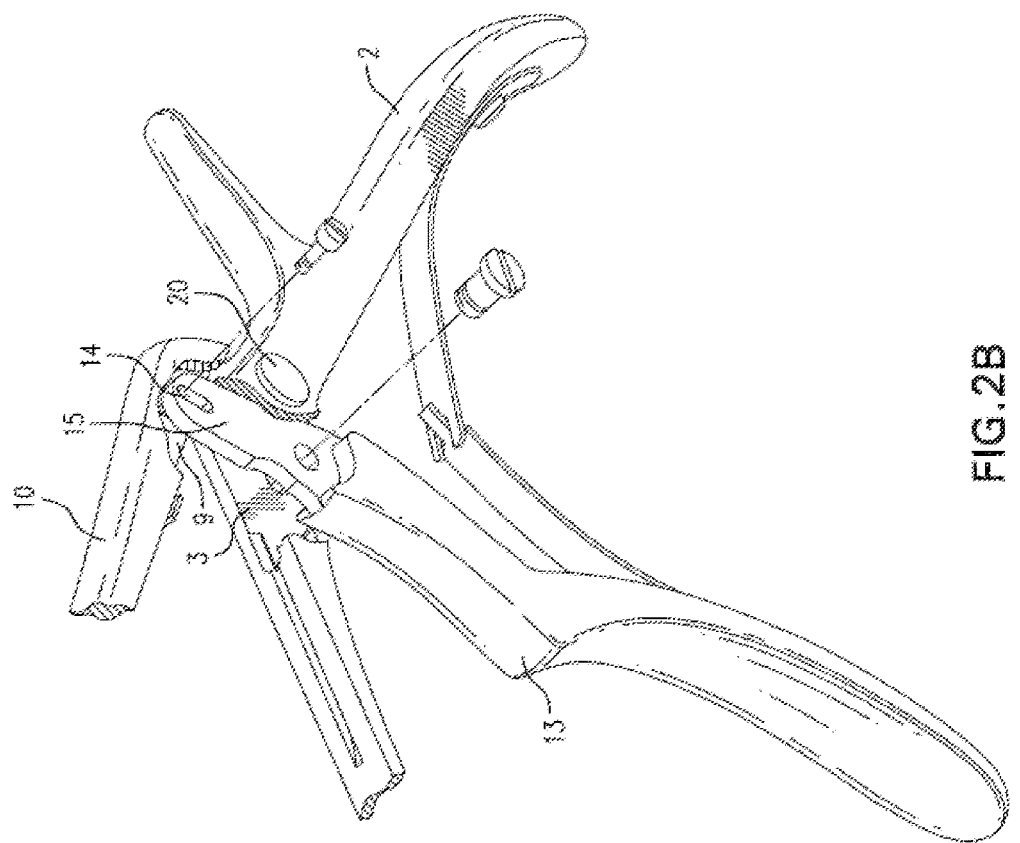
FIG. 2B is a cut away view of the cavity of the proximal end of the moveable top shaft of an embodiment of the Rongeur and of the slot of the fixed bottom shaft where it interacts with the front handle.
Figure 3A:
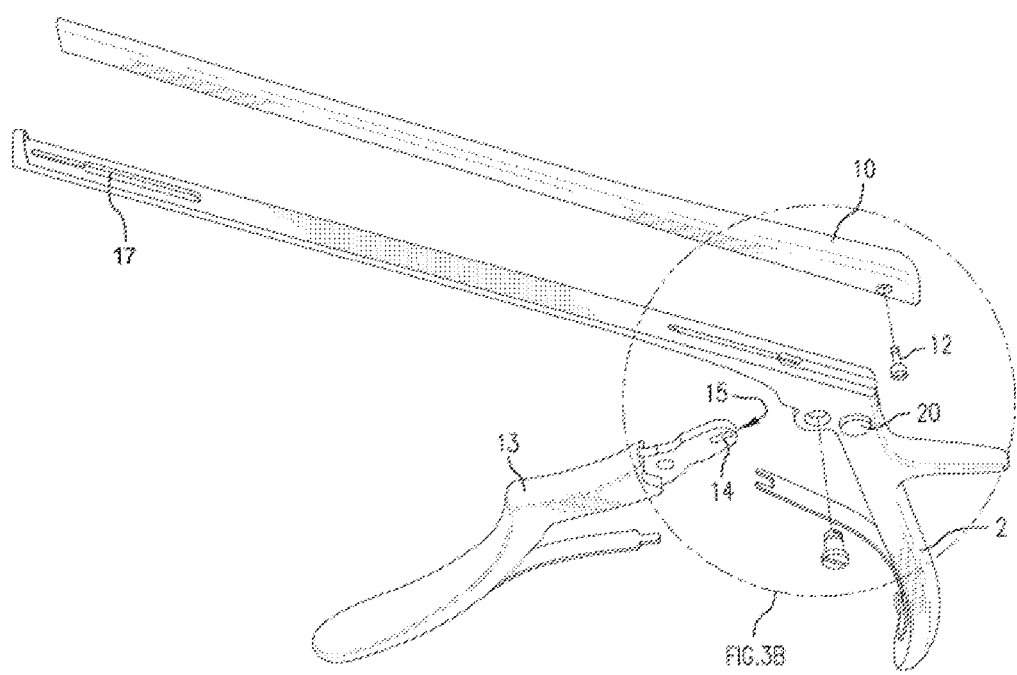
FIG. 3A is an exploded view of the parts of an embodiment of the Rongeur.
Figure 3B:
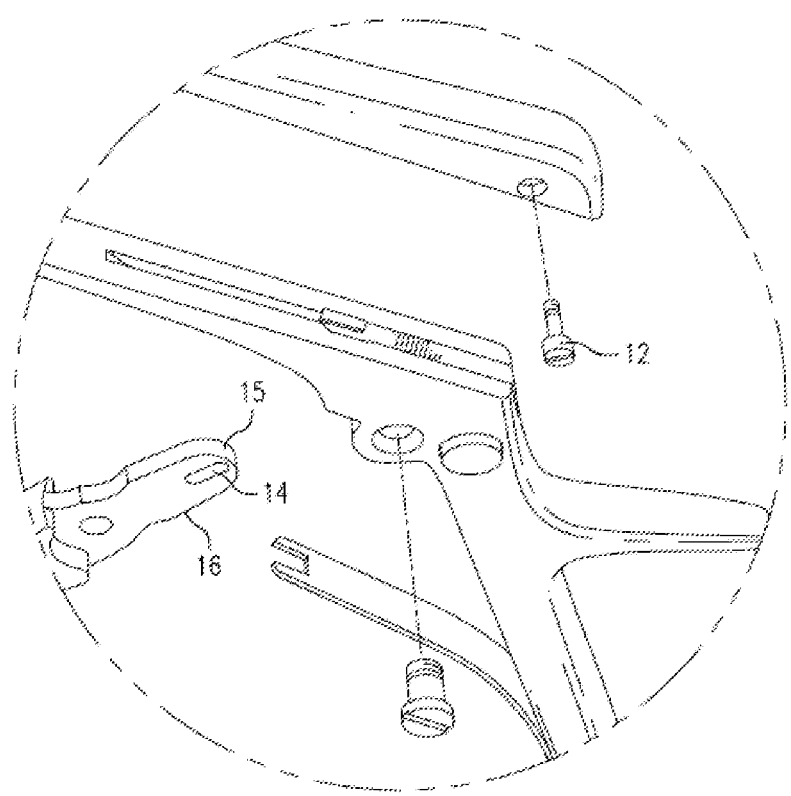
FIG. 3B is an enlarged exploded view the parts of an embodiment of the Rongeur.

Depicted in FIG. 3A, front handle (13) has a proximal end (15) containing drive hole (14) and a distal end forming front handle (13) of the Rongeur. Turning to FIG. 2B, the proximal end (15) of front handle (13) is fitted through slot (3) of fixed bottom shaft (1) and into cavity (9) of top shaft (10) whereby drive hole (14) receives drive pin (12). In this simple design, once the Rongeur is assembled, drive pin (12) is never released from drive hole (14) during the use of the Rongeur in a medical procedure or thereafter in an activated position during cleaning and sterilization. FIGS. 3A and 3B further show the parts of the push button Rongeur. The proximal end (15) of front handle (13) has rear surface (16) which contacts actuator shaft (23) (shown in FIG. 4) when the push button actuator (20) is in normal position and ready for use.

Figure 4:
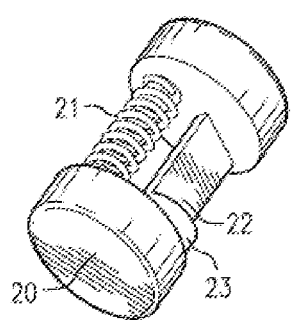
FIG. 4 is a perspective view of the push button actuator of the Rongeur.

FIG. 4 shows the structure of push button actuator (20). Push button actuator (20) is comprised of a compression spring (21) and shaft (23) containing groove (22).

Figure 5:
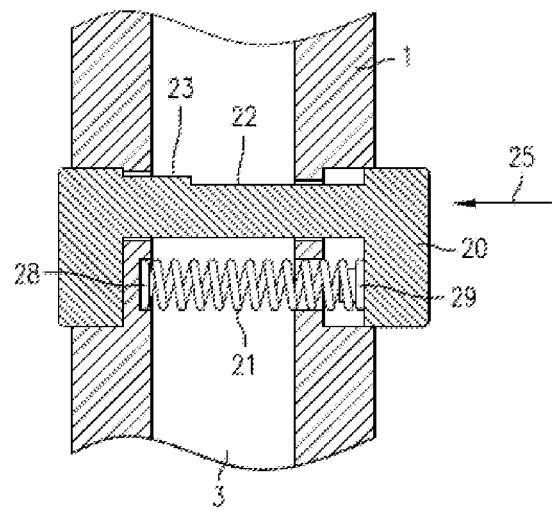
FIG. 5 is a cross sectional view of the push button actuator in the Rongeur.

Shown in FIG. 5 is a cross section of the push button actuator (20) in normal position before actuation. The push button actuator (20) is operably connected to fixed bottom shaft (1). Compression spring 21 has a distal end (28) attached to an inner wall in slot (3) of fixed bottom shaft (1) and a proximal end (29) contacting push button actuator (20). Before activation, compression spring (21) is extended holding push button actuator (20) in its normal position. Push button actuator (20) is depressed to an activated position (not shown) by pushing push button actuator (20) toward fixed bottom shaft (1) [the direction shown by arrow (25)], thereby compressing compression spring (21). On actuation of push button actuator (20), rear surface (16) of front handle (13) (FIG. 3B) slips into groove (22), thereby allowing top shaft (10), which is engaged with drive pin (12) through drive hole (14) in the proximal end of front handle (13), to be slightly retracted from the outer circumference of shaft (23), to contact the surface of groove (22). Top shaft (10) may then be separated from fixed bottom shaft (1) to an angle (40) (shown in FIG. 2). The separation of top shaft (10) from fixed bottom shaft (1) to angle (40) makes the parts of the Rongeur readily accessible for cleaning and sterilization. This separation of the long parts to angle (40) is facilitated by the movement of drive pin (12) within drive hole (14) which is elongated to accommodate the movement of drive pin (12). Drive pin (12) remains captured by drive hole (14) at all times while the Rongeur is in use and while is long parts are separated for cleaning.

After cleaning, top shaft (10) is returned to contact with fixed bottom shaft (1), compression spring (21) returns push button actuator (20) to its normal position, and the Rongeur is ready for use (FIG. 1). When ready for use, top shaft (10) is slideably connected to fixed bottom shaft (1) and held in a forward position by the contact of rear surface (16) of front handle (13) (FIG. 3B) with shaft (23) of push button activator (20) (FIGS. 4 and 5).

The foregoing detail of the disclosed embodiment of the push button Rongeur is not intended as a limitation on other configurations of the push button actuator which may be apparent to those skilled in the art without departing from the scope and spirit of the disclosed invention as defined in the following claims.

What is claimed is:

1. A Rongeur comprising:
a top shaft with a proximal end having a cutting edge and a distal end hingedly connected to a front handle, the top shaft configured for sliding engagement with a bottom shaft having a rear handle at a distal end when in a closed position, and to hinge open at the hinged connection when in a released position;
the front handle pivotally connected to the rear handle and configured for a retracted position, a first extended position, and a second extended position;
the retracted position configured to slide the top shaft proximally such that the cutting edge approaches a proximal end of the bottom shaft;
the first extended position configured to slide the top shaft distally a first distance;
the second extended position configured to slide the top shaft distally a second distance greater than the first distance and position the top shaft into the released position; and
a push button actuator having a biased position and an actuated position, the biased position configured to block the second extended position, the actuated position configured to permit the second extended position.

2. The Rongeur of claim 1, wherein one of the top shaft and the bottom shaft comprises at least one slot configured to receive a corresponding protrusion, and the other of the top shaft and the bottom shaft comprises the corresponding protrusion; wherein the corresponding protrusion is configured to slidably mate with the slot when the top shaft is in the closed position.

3. The Rongeur of claim 2, wherein the protrusion is T-shaped.

4. The Rongeur of claim 1, wherein the push button actuator comprises a groove configured to receive a portion of the front handle when in the actuated position.

5. The Rongeur of claim 1, wherein the front handle comprises a drive hole on its proximal end, wherein the drive hole is elongated to allow movement of a drive pin attached to the top shaft while the top shaft is in the released position, thereby permitting the top shaft to hinge open to at least an acute angle from the bottom shaft when the push button actuator is in the actuated position.

6. The Rongeur of claim 5, wherein the drive pin remains within the drive hole while the Rongeur is in use and when the top shaft is separated from the bottom shaft for cleaning and sterilization.

7. The Rongeur of claim 1, wherein the push button actuator further comprises a compression spring which maintains the push button actuator in a normal position while the Rongeur is in use and which is depressed to activate the push button actuator.

8. A Rongeur comprising:
a top shaft with a proximal end having a cutting edge and a distal end hingedly connected to a front handle, the top shaft configured for sliding engagement with a bottom shaft having a rear handle at a distal end when in a closed position, and to hinge open at the hinged connection when in a released position;
the front handle pivotally connected to the rear handle and configured for a retracted position, a first extended position, and a second extended position;
the retracted position configured to slide the top shaft proximally such that the cutting edge approaches a proximal end of the bottom shaft;
the first extended position configured to slide the top shaft distally a first distance;
the second extended position configured to slide the top shaft distally a second distance greater than the first distance and position the top shaft into the released position;
a push button actuator having a biased position and an actuated position, the biased position configured to block the second extended position, the actuated position configured to permit the second extended position; and
one of the top shaft and the bottom shaft comprises a slot configured to receive a corresponding protrusion, and the other of the top shaft and the bottom shaft comprises the corresponding protrusion;
wherein the corresponding protrusion is configured to slidably mate with the slot when the top shaft is in the closed position.

9. The Rongeur of claim 8, wherein the push button actuator further comprises a compression spring which maintains the push button actuator in a normal position while the Rongeur is in use and which is depressed to activate the push button actuator.

10. The Rongeur of claim 8, wherein the corresponding protrusion is configured to release from the slot when the top shaft is in the released position.

11. The Rongeur of claim 10, wherein the slot comprises a wide region configured to allow the corresponding protrusion to release from the slot when the top shaft is in the released position and hinged open.

12. The Rongeur of claim 8, wherein the push button actuator further comprises a compression spring which maintains the push button actuator in a normal position while the Rongeur is in use and which is depressed to activate the push button actuator.

13. The Rongeur of claim 8, wherein the push button actuator comprises a groove configured to receive a portion of the front handle when in the actuated position.

14. The Rongeur of claim 8, wherein the front handle comprises a drive hole on its proximal end, wherein the drive hole is elongated to allow movement of a drive pin attached to the top shaft while the top shaft is in the released position, thereby permitting the top shaft to hinge open to at least an acute angle from the bottom shaft when the push button actuator is in the actuated position.

15. The Rongeur of claim 14, wherein the drive pin remains within the drive hole while the Rongeur is in use and when the top shaft is separated from the bottom shaft for cleaning and sterilization.

* * * * *